United States Patent [19]

Powell

[11] 4,031,087

[45] June 21, 1977

[54] 3,4,7,8-TETRAHYDRO-9-NITRO-7-SUBSTITUTED-2H,6H-PYRIMIDO-(4,3-B)(1,3)THIAZINES

[75] Inventor: James E. Powell, Modesto, Calif.

[73] Assignee: Shell Oil Company, Houston, Tex.

[22] Filed: June 27, 1975

[21] Appl. No.: 590,983

[52] U.S. Cl. ............................ 260/243 R; 424/246
[51] Int. Cl.² ........................................... C07D 279/08
[58] Field of Search ................. 260/243 R; 424/246

[56] References Cited

UNITED STATES PATENTS 3,932,395  1/1976  Mideg et al. ................. 260/243

*Primary Examiner*—John M. Ford

[57] ABSTRACT

Novel insecticidal 3,4,7,8-tetrahydro-9-nitro-7-substituted-2H,6H-pyrimido(4,3-b)(1,3)thiazines.

1 Claim, No Drawings

3,4,7,8-TETRAHYDRO-9-NITRO-7-SUBSTITUTED-2H,6H-PYRIMIDO-(4,3-B)(1,3)THIAZINES

DESCRIPTION OF THE INVENTION

It has been found that useful insecticidal activity is possessed by 3,4,7,8-tetrahydro-9-nitro-7-substituted-2H,6H-pyrimido(4,3-b) (1,3-thiazines of the formula

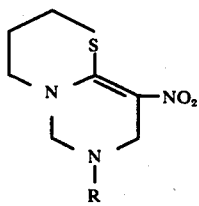

(A)

wherein R is

A. A moiety containing from one to thirty carbon atoms, selected from
1. alkyl;
2. alkyl substituted by one or more of
   a. halogen (particularly bromine, chlorine or iodine);
   b. cyano;
   c. cycloalkyl or alkylcycloalkyl in which the ring contains three to twelve carbon atoms;
   d. heterocyclic in which the ring contains five to seven atoms selected from carbon and one or two oxygen (—O—), sulfur (—S—) or nitrogen (=N— or —N ($R^2$)—) atoms, wherein $R^2$ is hydrogen or alkyl;
   e. aryl, optionally substituted on the ring by one of halogen (particularly bromine, chlorine or iodine), nitro, cyano, lower alkyl, lower alkoxy, lower alkylthio, amino (—N($R^3$) ($R^3$)) or phenoxy, $R^3$ being hydrogen, alkyl, hydroxyalkyl, or aryl or aralkyl optionally substituted as indicated above;
   f. hydroxyl, carboxy or alkoxycarbonyl;
   g. $R^3$ —O—, $R^3$—S—, $R^3$—S(O)—, $R^3$—S(O)$_2$—, $R^3$—C(O)— or $R^3$—O—C(O)—;
   h. —N($R^3$) ($R^4$) or —$R^5$—N($R^3$) ($R^4$) wherein $R^5$ is alkylene in which one or more carbon atoms has been replaced by nitrogen (—$NR^7$—) or oxygen (—O—) bonded to carbon, and $R^4$ is one of the moieties represented by $R^3$ or is —$R^6$ —N($R^7$) ($R^7$), wherein $R^6$ is alkylene or one of the moieties represented by $R^5$, and $R^7$ is one of the moieties represented by $R^3$ or $R^4$ or $R^7$ is:

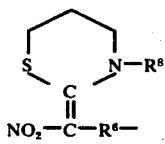

(a)

wherein $R^8$ is hydrogen, alkyl, alkenyl, alkylthioalkyl, alkoxyalkyl, cycloalkylalkyl, cyanoalkyl, haloalkyl, haloalkenyl, or aralkyl, as these moieties are described above or is:

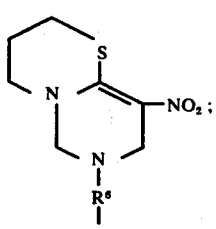

(b)

-continued

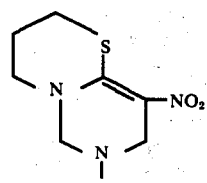

(3)

4. alkenyl, alkynyl or cycloalkyl, or any of these substituted is indicated for alkyl in (2), above;
5. aryl, particularly phenyl, optionally substituted as indicated above;

or is

B. —N($R^9$) ($R^9$) wherein $R^9$ is hydrogen, alkyl or alkanoyl of one to ten, preferably from one to four, carbon atoms; benzoyl or phenyl.

In these compounds, each aliphatic moiety can be straight-chain or branched-chain in configuration. Preferably, the moieties represented by the various R symbols contains no more than 10 carbon atoms each. The preferred aryl moiety is phenyl, with phenylmethyl and phenethyl being the preferred aralkyl moieties. Preferred heterocyclic moieties are furanyl, tetrahydrofuranyl, dioxolanyl, thienyl, thiopyranyl, pyridinyl, pyrrolidinyl and morpholino.

The invention also includes salts of such compounds, such as the hydrohalide, hydrosulfate, alkyl halide, alkyl sulfate, hydrotetrafluoroborate and alkyl tetrafluoroborate salts.

To illustrate the genus of compounds provided by the invention, preparation of typical individual species thereof is described hereinafter. Other, typical illustrative individual species are those wherein R represents the following moieties, this manner of naming these species being accurate, yet pointing out the differences among the different species more clearly than if the entire, complicated name of each species were to be given. Since the compounds of this invention can be prepared from primary amines, in cases where the identity of the primary amine is not known with certainty, as in cases of mixtures of amines, such the coco amines, soya amines and the like, R will be defined in terms of the particular amine:

R = butyl,
decyl
2-ethylhexyl
hexadecyl
hexyl
octadecyl
octyl
propyl
cyclopropyl
cyclobutyl
cyclodecyl
cyclododecyl
1-methylcyclopropyl
dihydroabietyl
alkyl of mixtures of tert-$C_{11-14}$ primary amines
alkyl of mixtures of tert-$C_{18-24}$ primary amines
alkyl of coco amines
alkyl of soya amines alkyl of hydrogenated tallow amines
1-cyclopropylethyl
propargyl
2-bromoethyl
2-(carboxyl)ethyl
1-(carboxy)ethyl
2-(ethoxycarbonyl)ethyl
1,2-di(carboxy)ethyl
3'-(carboxy)cyclohexylmethyl
1-(carboxyl)-2-(methyl)propyl
1-(hydroxymethyl)propyl
tris(hydroxymethyl)methyl
1,1-bis(hydroxymethyl)ethyl
2-(hydroxy)propyl
1-hydroxy-2,2,2-trichloroethyl
1-(methyl)-4-(diethylamino)butyl
2-(2-hydroxyethylamino)ethyl
2-(benzylamino)ethyl
2-(2-hydroxyethyl 2-aminoethylamino)ethyl
2-(3-(2-aminoethylamino)propyl)amino)ethyl
p-chlorobenzyl
2-(3,4-dimethoxyphenyl)ethyl
1-(carboxy)3-(amino)propyl
1(carboxy-3-(methylthio))propyl
p-methoxybenzyl
2-methylbenzyl
3-(methylthio)propyl
1(carboxy)-4-(amino)butyl
1-(carboxy)-2-(phenyl)-ethyl
α-carboxybenzyl
1-(carboxy)-2-(hydroxy)ethyl
2(4-hydroxyphenyl)ethyl
1-(ethoxycarbonyl)-2-(4-hydroxyphenyl)ethyl
1-(carboxy)-2-(benzylthio)ethyl
cyanomethyl
1-cyano-1-methylethyl
2-(cyano)-ethyl
2-(hydroxy)-2-(m-hydroxyphenyl)ethyl
1-(phenyl)-2-(hydroxy)propyl
2-(mercapto)ethyl
1-(phenyl)-2-(amino)propyl
3-(methylamino)propyl
1-(methyl)-2(phenyl)-2-(amino)ethyl
1(carboxy)3-(ethylthio)propyl
3-(2-ethylhexoxy)propyl
1-(carboxy)-2-(phenyl)ethyl
2-(hydroxy)-2-(phenyl)ethyl
1-(methyl)-2-(phenyl)ethyl
diphenylmethyl
1,1-dimethyl-2-(p-chlorophenyl)ethyl
1-(carboxy)-2-(3,5-dibromo-4-hydroxyphenyl)-ethyl
2-diphenylmethylene)butyl
1-(benzyl)ethyl
2-(1-naphthylamino)ethyl
1-(carboxy)-2-(methyl)-2-(mercapto)propyl
2-(phenyl)cyclopropyl
2-(1-piperazinyl)ethyl
2-(4-imidazolyl)ethyl
1(carboxy)-2-(4-imidazolyl)ethyl
3-(3-(3-aminopropoxy)-2,2-dimethylpropoxy)propyl
2-(aminomethyl)cyclopentyl
2-aminocyclopentylmethyl
4-(4-aminocyclohexylmethyl)cyclohexyl
2-(3-indolyl)ethyl
1-(ethyl)-2-(2-thienyl)ethyl
1-(ethyl)-2-(3-indolyl)ethyl
2-(3-pyrazolyl)ethyl
2-(2-naphthalenyl)imidazolin-1-yl)ethyl
2-(4-morpholinyl)ethyl
1-(cyclopropyl)-1-(cyano)ethyl
3-(phenyl)allyl
5-(phenyl)--2,4-pentadienyl
3-chloroallyl
3-(4-(3-aminopropoxy)butoxy)propyl
amino
methylamino
acetamido
benzamido
phenylamino The compounds of this invention can be prepared conveniently by treating an alcoholic (preferably ethanolic) solution of tetrahydro-2-(nitromethylene)-2H-1,3-thiazine (I, following) with an aqueous solution of the appropriate primary amine or hydrazine with aqueous formaldehyde. Preparation of I is shown in Example 1, hereinafter. Preferably, the treatments are conducted at low temperature (e.g., 5°–10°) and the formaldehyde is added to the stirred mixture of I and amine. In some cases, it may be desirable to employ as catalyst a small amount of a strong non-oxidizing mineral acid, such as concentrated hydrochloric acid. As illustrated in the examples set forth hereinafter, the product is recovered and purified by conventional work-up procedures.

These methods for preparing, isolating and purifying the compounds of this invention are illustrated in the following examples of the preparation of particular species thereof. In all cases, the identity of the product was confirmed by elemental analysis and by infrared and nuclear magnetic resonance spectrum analyses. Because of the length and complexity of the nomenclature involved, the compounds prepared in these examples are defined in terms of Formula A, page 1, of this specification, the title in each example defining the identity of the moiety R.

EXAMPLE 1 - R = phenylmethyl (1)

A. Preparation of ethyl nitro(tetrahydro-2H1,3-thiazin-2-ylidene)acetate (1a)

To a mixture of 235 g of 5,6-dihydro-2-(methylthio)-4H-1,3-thiazine (A. F. McKay, et al., J. Am. Chem. Soc., 80, 3339 (1958) and 2 g of zinc chloride, at approximately 115° in a nitrogen atmosphere, 263 g of ethyl nitroacetate (S. Zea, et. al., Kogyo Kagaku Zasshi, 74, 70 (1971) was added dropwise over a 1.5 hour period. The mixture was held at 110°–120°. When evolution of methyl mercaptan ceased after 45 minutes further stirring of the heated mixture, 1 g of zinc chloride was added and the mixture was stirred at about 115° for 1.25 hours. An additional 1 g of zinc chloride was added and stirring of the mixture at about 115° was continued for 1.5 hours. The mixture then was poured into a cooled solution of 2/1 ether/isopropyl alcohol mixture. The crystallized product was collected, washed with ether and dried under reduced pressure to leave a tan solid, m.p. 100°–102°, which on recrystallization from methanol gave 1A as a pale yellow solid, m.p. 105°–106°.

b. Preparation of I 2.3 g of 1A was added to 10 ml of 20% aqueous sodium hydroxide and the mixture was stirred at room temperature for 12 hours. The resulting solution was treated dropwise with 3.5 g of acetic acid. The addition was accompanied by vigorous gas evolution. The resulting mixture was extracted with methylene chloride and the extract was dried (magnesium sulfate) and concentrated under reduced pressure to give I as a pale yellow solid, m.p. 76°–78°.

c. Preparation of 1

A mixture of 15.0 g of benzylamine and 35 ml of water was added to a cold (ca 10°) mixture of 20.0 g of I and 60 ml of ethanol. Then at 5°–10°, 23.0 g of formaldehyde (37% in water) was added dropwise to the stirred mixture over a period of 1.5 hours. The mixture was allowed to stir overnight at room temperature, diluted with water and extracted with methylene chloride. The organic phase was separated, washed with water, dried with sodium sulfate and stripped of solvent under reduced pressure. The residue was crystallized and recrystallized from ethyl acetate to yield 1, as a light yellow solid, m.p.: 153°–155.5°.

EXAMPLE 2 - R = cyclooctyl (2)

3.6 of cyclooctyl amine in 7 ml of water was added in portions to a stirred cold (10°) solution/suspension of 4.0 g of I in 12 ml of ethyl alcohol. 4.6 g of 37% aqueous formaldehyde then was added dropwise to the stirred cold mixture. The stirred mixture then was allowed to warm to room temperature. Immediately a precipitate formed. This was collected, washed with isopropyl alcohol, ether and then air dried to give 2, as a yellow solid, m.p.: 146°–147°.

By the procedures described in Example 1 and 2, the following further individual species of the compounds of this invention were prepared from I and the appropriate amine.

| Example | Compound | R = | Melting Point (°) |
|---|---|---|---|
| 3 | 3 | methyl | 160–162.5 |
| 4 | 4 | tert-butyl | 125–127 |
| 5 | 5 | isopropyl | 159.5–160 |
| 6 | 6 | allyl | 127–129 |
| 7 | 7 | 2-furanylmethyl | 150–152 |
| 8 | 8 | cyclohexyl | 151–152.5 |
| 9 | 9 | ethyl | 129–131.5 |
| 10 | 10 | phenyl | 160–162.5 |
| 11 | 11 | 2-methoxyethyl | 102–104 |
| 12 | 12 | 2-phenethyl | 161.5–162 |
| 13 | 13 | ethoxycarbonylmethyl | 196.5–197 |
| 14 | 14 | 4-methoxyphenyl | 156–158 |
| 15 | 15 | 3,4,7,8-tetrahydro-9-nitro-2H,6H-pyrimido-(4,3-b)-1,3-thiazin-7-yl | 156–158 |
| 16 | 16 | 2-(methylthio)ethyl | 93–95 |
| 17 | 17 | carboxymethyl | 162–163 (dec) |
| 18 | 18 | 3-chlorophenyl | 177–178 |
| 19 | 19 | 3-chlorobenzyl | 195–196 |
| 20 | 20 | 2-chlorobenzyl | 154–156 |
| 21 | 21 | 4-methylcyclohexyl (cis) | 172–173 |
| 22 | 22 | 1-phenylethyl | 150–151.5 |
| 23 | 23 | 1-phenylethyl (R-isomer) | 143–144.5 |
| 24 | 24 | 1-phenylethyl (S-isomer) | 143–145 |
| 25 | 25 | 4-methylcyclohexyl (trans) | 131.5–134 |

Salts of the invention were prepared as follows:

EXAMPLE 26 - R = cyclohexyl, HCl salt (26)

2.0 g of hydrogen chloride gas was bubbled into a stirred cold (25°) mixture of 4.5 g of 8 in 80 ml of methylene chloride. The mixture was stirred for an additional 15 minutes, then filtered. The solid was washed with petroleum ether and recrystallized from methanol/ether to yield 26, as a light yellow solid, m.p.: 168°–169°.

By this procedure were prepared other HCl salts:

| Example | Compound | R = | Melting Point (°) |
|---|---|---|---|
| 27 | 27 | ethyl | 162–162 |
| 28 | 28 | 2-(methoxy)ethyl | 157–157.5 |

EXAMPLE 29 - R = dimethylamino (29)

To a cold (ca 10°) solution of 4.0 g of (I) in 12 ml of ethyl alcohol was added, in several portions, 1.7 g of 1,1-dimethylhydrazine and 0.2 ml of concentrated hydrochloric acid in 7 ml of water. To this mixture, at 5°–10°, 4.6 g of 37% aqueous formaldehyde was added dropwise. The cold mixture was stirred for about 2 hours, then was stirred at room temperature overnight. The reaction mixture was taken up in methylene chloride, washed with saturated sodium bicarbonate solution, then with saturated sodium chloride solution and dried over sodium sulfate. The solvent was evaporated under reduced pressure and the residue was triturated with ether to give a light orange solid. This was recrystallized with ethyl acetate to give 29, as a yellow solid, m.p.: 112.5°–113.°.

Compounds of this invention exhibit useful insecticidal activity, being of particular interest for control of the larval "caterpillar" or "worm" forms of insects of the genus Heliothis, such as H. zea (corn earworm, cotton bollworm, tomato fruitworm), H. virescens (tobacco budworm) the genus Agrotis, such as A. ipsilon (black cutworm). Some are also of interest for controlling pea aphids. In tests that have been conducted they have exhibited no toxicity to the 2-spotted spider mite and slight toxicity to mosquito larvae and houseflies. At least compounds 4 and 10 act rapidly, providing "quick knock-down" of corn earworm larvae.

Activity of compounds of this invention with respect to insects was determined by using standardized test methods to establish the $LC_{50}$ dosage (in milligrams of test compound per 100 milliliters of solvent or liquid carrier required in the solution or suspension of test compound used) to kill 50% of the test insects. The test insects were the housefly, corn earworm, mosquito, pea aphid and 2-spotted spider mite. Activity with respect to mosquito larvae was determined by placing the larvae in water containing the test compound.

All of compounds 1 through 26 were active with respect to the corn earworm. Compounds 2, 3, 7, 13, 16, 17 and 23–25 had low activity with respect to the housefly. All of the compounds except compounds 11, 12, 15 and 18–20 had low to moderate activity with respect to the pea aphid. All of the compounds except compounds 6, 10, and 12 were slightly active with respect to mosquito larvae. None was active with respect to the spider mite.

In the course of these tests it was noted that compounds 4 and 10 acted quickly on corn earworms, and compound 4 acted quickly upon pea aphids.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material, which may be inorganic or organic and of synthetic or natural origin, with which the active compound is mixed or formulated to facilitate its application to the plant, seed, soil or other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols, bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, mthyl ethyl ketone, methyl isobutyl ketone and cyclohexanone; ethers; aromatic hydrocarbons such as benzene, toluene and xylene; petroleum fractions such as kerosene, light mineral oils, chlorinated hydrocarbons, such as carbon tetrachloride, perchloroethylene, trichloroethane, including liquefied normally varporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentacerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75% w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½-10%w of toxicant. Granules may be manufactured by agglomeration or impregnation techniques. Generally, granules will contain ½-25%w toxicant and 0-10%w of additives such as stabilizers, slow release modifiers and binding agents. Emulsifiable concentrates usually contain, in addition to the solvent, and when necessary, co-solvent, 10--50%w/v toxicant, 2-20%w/v emulsifiers and 0-20%w/v of appropriate additives such as stabilizers, penetrants and corrosion inhibitors. Suspension concentrates are compounded so as to obtain a stable, non-sedimenting, flowable product and usually contain 10-75%w toxicant, 0-5%w of dispersing agents, 0.1-10%w of suspending agents such as protective colloids and thixotropic agents, 0-10%w of appropriate additives such as defoamers, corrosion inhibitors, stabilizers, penetrates and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the loucs to be protected — i.e. the dosage to which the insect contacts — is of the order of 0.001% to 0.5% based on the total weight of the formulations, though under some circumstances the effective concentration will be as little as 0.0001% or as much as 2%, on the same basis.

I claim as my invention:

1. A compound of the formula

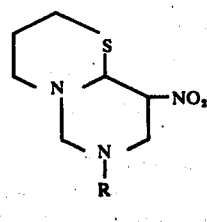

wherein R is

A. A moiety containing one to thirty carbon atoms, which is one of 1. alkyl;
2. alkyl substituted by one or more of
   a. halogen;
   b. cyano;
   c. cycloalkyl or alkylcycloalkyl in which the ring contains three to twelve carbon atoms;
   d. furanyl, tetrahydrofuranyl, dioxolanyl, thienyl, thiopyranyl, pyridinyl, pyrrolidinyl and morpholino;
   e. phenyl, optionally substituted on the ring by one of bromine, chlorine or iodine, nitro, cyano lower alkyl, lower alkoxy, lower alkylthio, amino ($-N(R^3)$ $(R^3)$) or phenoxy, $R^3$ being hydrogen, alkyl, hydroxyalkyl, or phenyl or phenalkyl optionally substituted as indicated above;
   f. hydroxyl, carboxy or alkoxycarbony;
   g. $R^3$ —O—, $R^3$—S—, $R^3$—S(O)—, $R^3$ —S(O)$_2$—, $R^3$—C(O)— or $R^3$—O—C(O)—;
   h. —N($R^3$) ($R^4$) or —$R^5$—N($R^3$) ($R^4$) wherein $R^5$ is alkylene in which one or more carbon atoms has been replaced by nitrogen (—N$R^7$—) or oxygen (—O—) bonded to carbon, and $R^4$ is one of the moieties represented by $R^3$ or is —$R^6$ —N($R^7$) ($R^7$), wherein $R^6$ is alkylene or one of the moieties repesented by $R^5$, and $R^7$ is one of the moieties represented by $R^3$ or $R^4$ or $R^7$ is:

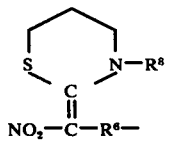
(a)

wherein $R^8$ is hydrogen, alkyl, alkenyl, alkythioalkyl, alkoxyalkyl, cycloalkylalkyl, cyanoalkyl, haloalkyl, haloalkenyl, or phenalkyl, as these moieties are described above or is:

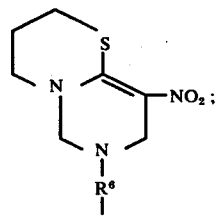
(b)

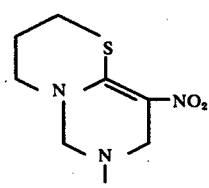
(3)

4. alkenyl, alkynyl or cycloalkyl, or any of these substituted as indicated for alkyl in (2), above;
5. phenyl, optionally substituted as indicated above; or is B. —N($R^9$) ($R^9$) wherein $R^9$ is hydrogen alkyl or alkanoyl of one to ten carbon atoms; benzoyl or phenyl and salts of such compound.

* * * * *

UNITED STATES PATENT AND TRADEMARK OFFICE
CERTIFICATE OF CORRECTION

PATENT NO. : 4,031,087
DATED : June 21, 1977
INVENTOR(S) : JAMES E. POWELL

It is certified that error appears in the above-identified patent and that said Letters Patent are hereby corrected as shown below:

Column 8, Claim 1,
Change the first structural formula from

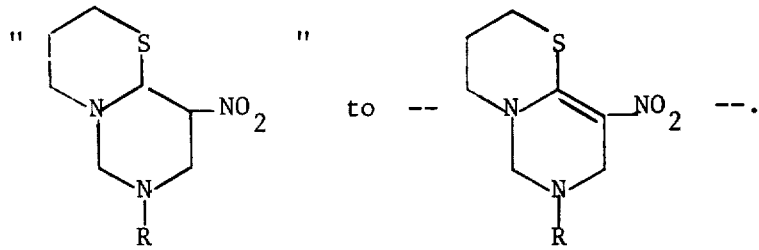

Column 9, line 11, place a comma after "cyano".

Column 9, line 17, change "alkoxycarbony" to -- alkoxycarbonyl --.

Column 10, line 30, place a comma after "hydrogen".

Column 10, last line, place a comma after "phenyl".

Signed and Sealed this

Sixth Day of December 1977

[SEAL]

Attest:

RUTH C. MASON
*Attesting Officer*

LUTRELLE F. PARKER
*Acting Commissioner of Patents and Trademarks*